United States Patent [19]
Teissier et al.

[11] Patent Number: 6,046,366
[45] Date of Patent: Apr. 4, 2000

[54] PREPARATION OF β-HYDROXYCARBONYL AND/OR α,β-UNSATURATED CARBONYL COMPOUNDS

[75] Inventors: Rémy Teissier, Francheville; Didier Tichit, Montpellier Cedex, both of France

[73] Assignee: Elf Atochem S.A., Puteaux, France

[21] Appl. No.: 09/206,296

[22] Filed: Dec. 7, 1998

[30] Foreign Application Priority Data

Dec. 5, 1997 [FR] France .................................. 97 15390

[51] Int. Cl.[7] .................................. C07C 45/45
[52] U.S. Cl. .................. 568/388; 568/390; 568/463
[58] Field of Search .................. 568/388, 390, 568/463

[56] References Cited

U.S. PATENT DOCUMENTS 5,254,743 10/1993 Holmgren et al. .................. 568/463
5,672,764 9/1997 Teissier et al. .................. 568/388

FOREIGN PATENT DOCUMENTS 0 095 783 12/1983 European Pat. Off. .
92/00266 1/1992 WIPO .

OTHER PUBLICATIONS

XP–000610152, Aldol condensation of acetaldehyde using calcined layered double hydroxides, Kagunya et al., Applied Clay Science, vol. 10 (1995) pp. 95–102.

XP–002072416, Catalytic Reactions by Thermally Activated, Synthetic, Anionic Clay Minerals, Walter T. Reichle, Academic Press, Inc. (1985) pp. 547–557.

XP–002072417, Aldol Condensation Reaction between Formaldehyde and Acetone over Heat–Treated Synthetic Hydrotalcine and Hydrotalcite–Like Compounds, The Chemical Society of Japan, vol. 61, No. 3 (1988) pp. 1008–1010.

*Primary Examiner*—Sreeni Padmanabhan
*Attorney, Agent, or Firm*—Millen, White, Zelano & Branigan, P.C.

[57] ABSTRACT

The invention relates to the use of compounds of formula:

$$[M(II)_{1-x}M^*(III)_x(OH)_{2+x}] \cdot mH_2O \qquad (I)$$

in which M(II) represents a divalent cation chosen from the group consisting of nickel, zinc, cobalt, magnesium or the mixture of two or more of the abovementioned metals; M(III) represents a trivalent cation, such as aluminum, gallium, iron or chromium, with the exception of the compound of formula (I) in which M(II) is magnesium and M(III) is aluminum, x is between 0.20 and 0.33 and $m \leq 1$; in the preparation of β-hydroxycarbonyl and/or α,β-unsaturated carbonyl compounds.

11 Claims, No Drawings

PREPARATION OF β-HYDROXYCARBONYL AND/OR α,β-UNSATURATED CARBONYL COMPOUNDS

The present invention relates to the use of compounds with a structure of hydrotalcite (HTLC) type in the preparation of β-hydroxycarbonyl and/or α,β-unsaturated carbonyl compounds by basic heterogeneous catalysis.

These compounds are generally obtained industrially by aldolization and/or aldolization/crotonization of an aldehyde and/or of a ketone in the presence of a basic catalyst, such as dilute sodium hydroxide or potassium hydroxide solutions.

However, the use of such catalysts in so-called homogeneous-catalysis processes exhibits numerous disadvantages. In particular, before separating the products formed from the reaction mixture, it is necessary to remove the basic catalyst by neutralization with an acid, such as $H_3PO_4$, precipitation of the salts obtained and filtration. During these treatments, it is impossible to avoid encrusting the distillation columns with the salts resulting from the neutralization, which results in the plant being regularly shut down in order to clean the columns.

In order to overcome these disadvantages, various authors have proposed operating under solid basic heterogeneous catalysis with a solid which can easily be separated from the organic phase, which allows the process to be simplified and no effluents to be produced originating from the neutralization of sodium hydroxide.

Thus it is that Geng Zhang et al., Applied catalysis, 36 (1988) 189–197, have studied the aldolization of acetone catalysed by solid basic catalysis, such as MgO, CaO, SrO, BaO, lanthanum(III) oxide $La_2O_3$ and $ZrO_2$.

These authors have found that the activities of these catalysts, based on the same unit of specific surface, were, in order: $BaO>SrO>CaO>MgO>La_2O_3>ZrO_2$. Furthermore, for MgO, the addition of water and of ammonia by preabsorption resulted in a marked increase in the activity and in the selectivity for the production of DAA.

Kozo Tanabe et al., Applied Catalysis, 48 (1989) 63–70, have studied the addition of metal cations to magnesium oxide in order to obtain a catalyst for the aldolization of acetone. The influence of the $Na^+$, $K^+$, $Rb^+$, $Cs^-$, $Al^{3+}$, $Mn^{2+}$, $Fe^{3+}$, $Co^{2-}$, $Ni^{2+}$, $Cu^{2+}$, $Zn^{2+}$ and $Zr^{4-}$ cations was studied. These authors noticed that the $Na^-$, $Zr^{4+}$ and $Zn^{2+}$ cations effectively increased the catalytic activity for a content by weight of 0.5 to 1% of the metal cation. The addition of appropriate amounts of water increased both the activities and the selectivities of these MgO catalysts doped using these cations. On the other hand, these authors demonstrated that the addition of $Al^{3+}$ in any concentration caused a decrease in the activity and this decrease proceeded in the same direction as the increase in the $Al^{3+}$ content, the range studied for $Al^{3+}$ varying between 0% and approximately 3% of $Al^{3+}$ by weight.

U.S. Pat. No. 5,144,089 discloses a liquid-phase aldol condensation process, in particular the conversion of butanal to 2-ethayl-2-hexenal in the presence of a solid catalyst. The catalyst is a solid magnesium oxide and aluminium oxide solution, which solution is derived from a hydrotalcite and has a specific surface of greater than 250 $m^2/g$.

French Patent FR 2,729,137 discloses a process for the selective aldolization of acetone to diacetone alcohol in the presence of a solid basic catalyst of formula:

$$[(Mg^{2+})_{1-x}(Al^{3+})_x(OH^-)_{2+x}].mH_2O$$

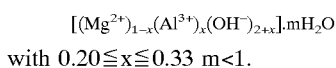

These catalysts make possible good conversion to diacetone alcohol, which virtually equals the value at thermodynamic equilibrium at 0° C.

It has now been found that it is possible to obtain β-hydroxycarbonyl and/or α,β-unsaturated carbonyl compounds with high conversions by using, as basic catalyst, a compound of formula:

$$[M(II)_{1-x}M(III)_x(OH)_{2+x}].mH_2O \qquad (I)$$

in which M(II) represents a divalent cation of the metals chosen from the group consisting of nickel, zinc, cobalt, magnesium or the mixture of at least two of the abovementioned metals, M(III) represents a trivalent cation of the metals chosen from the group consisting of aluminium, iron, gallium and chromium, with the exception of the compound of formula (I) in which M(II) is magnesium and M(III) is aluminium, $0.20 \leq x \leq 0.33$ and $m \leq 1$.

According to the present invention, it is preferable to use compounds of formula (I) in which M(II) is nickel or zinc and M(III) is aluminium or gallium.

According to the present invention, it is also preferable to use a compound of formula (I) in which M(II) is magnesium and M(III) is gallium.

These compounds can be prepared according to a protocol equivalent to that disclosed in Patent FR 2,729,137, incorporated in the present invention by reference.

In a first stage, an inorganic compound of synthetic hydrotalcite type of formula:

$$M(II)_{1-x}M(III)_x(OH)_2(CO_3)_{x/2}.mH_2O$$

is prepared according to known methods derived from the methods developed by S. Myata (Clay and Clay Minerals, 1980, 28, pages 50–56) or Reichle (EP 95783).

It involves coprecipitating a salt of the divalent metal with a salt of the trivalent metal in a solution at controlled and alkaline pH: $8<pH<11$. The pH is adjusted by virtue of a sodium carbonate and/or sodium hydroxide solution.

To complete the precipitation, the gel can be heated at reflux for several hours and the solid is separated by filtration, washed and dried.

The solid thus obtained comprises, as intercalated anion, in particular $CO_3^{2-}$ and other inorganic anions of the salts used for the synthesis, such as $Cl^-$, $NO_3^-$ or $SO_4^{2-}$. The latter are removed by exchange with $CO_3^{2-}$ in aqueous medium.

The product thus exchanged must contain, as intercalated anion, only carbonate (confirmed by chemical analysis).

This solid is calcined under a dry gas stream, generally air, for a period of time of between 2 h and 36 h, preferably 8 h and 15 h, at a temperature at most equal to 800° C. and preferably of between 400° C. and 600° C. The calcination temperature depends on the chemical nature of the solid, that is to say the nature of the metals. It is chosen for each solid with respect to two criteria:

- production of the amorphous mixed oxide devoid of the carbonate anion,
- possibility of rebuilding the structure.

This is because, if calcination is carried out at an excessively high temperature, there is separation between the phases of the oxide of the divalent metal and of the oxide of the trivalent metal. This separation may be invisible by X-ray diffraction and may only be seen during the rebuilding of the lamellar structure.

The calcined product is subsequently subjected to a stage of rehydration, the aim of which is to rebuild the lamellar structure.

This stage is carried out in the presence of water. This amount is always less than the theoretical amount for neutralizing the positive charges of the sheets. Each M(III) atom contributes one positive charge. More specifically, the rehydration reaction can be written in the following way:

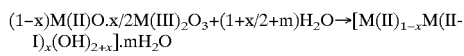

$(1-x)M(II)O.x/2M(III)_2O_3 + (1+x/2+m)H_2O \rightarrow [M(II)_{1-x}M(III)_x(OH)_{2+x}].mH_2O$ The rehydration is carried out at a temperature of between 0° C. and 200° C. Beyond 100° C., the rehydration is carried out in an autoclave under autogenous pressure or under a starting nitrogen pressure, at room temperature, of between 1 bar and 10 bar.

It is carried out over a time period of between half an hour and 120 h, according to the difficulty of rebuilding the lamellar structure.

The water necessary for the rebuilding can be in gaseous form. The rehydration can be carried out in a traversed stationary bed or in a fluidized bed. The flow rates are obviously different. The rehydration time is also different. The gas flow rate is variable, depending on the amount of solid to be activated.

The rehydration water can be in liquid form. It is then a case of treating the solid, an amorphous mixed oxide, with water. Either a suspension of solid in water is prepared or the solid is left under water.

The kinetics of rehydration depend on the temperature of the medium, on the stirring, on the particle size of the solid and on the nature of the metals constituting the solid. Thus, the rehydration can be completed in one hour or several days.

This is because a mixed magnesium-gallium oxide hydrates in one hour at 60° C.; its zinc-aluminium homologue hydrates at 80° C. in 8 hours; a mixed nickel-aluminium oxide, in order to be partially rehydrated, needs to be treated at 120° C. for 48 hours.

If the X-ray diffraction spectrum of the various solids is run, there is found:
  before calcination, the spectrum of a hydrotalcite,
  after calcination, the disappearance of the lines characteristic of the hydrotalcite structure and the appearance of the broad and not very intense line of the amorphous oxide of the divalent metal,
  after rehydration, the reappearance of the lines of the hydrotalcite structure and the decrease, indeed in the best cases the disappearance, of the line of the oxide of the divalent metal.

The compounds of formula (I) are used in the preparation of β-hydroxycarbonyl and/or α,β-unsaturated carbonyl compounds by basic catalysis.

To this end, an aldehyde of general formula $R^1$—CHO, in which $R^1$ represents a linear or branched alkyl radical comprising from 1 to 10 carbon atoms, can be reacted with itself in the presence of a compound of formula (I) or with at least one compound chosen from another aldehyde of general formula $R^2$—CHO, in which $R^2$ represents a hydrogen atom, a linear or branched or cyclic alkyl radical comprising from 1 to 10 carbon atoms, a phenyl radical, a benzyl radical or an aralkyl radical, and/or with a ketone of general formula $R^5$—CO—$R^6$, in which $R^5$ and $R^6$, which are identical or different, each represent a linear or branched alkyl radical comprising from 1 to 10 carbon atoms, which radicals can be connected to one another in order to form a ring.

A ketone of general formula $R^3$—CO—$R^4$, in which $R^3$ and $R^4$, which are identical or different, each represent a linear or branched alkyl radical comprising from 1 to 10 carbon atoms, can also be reacted with itself in the presence of a compound of formula (I) or else with at least one compound chosen from an aldehyde of general formula $R^2$—CHO, in which $R^2$ has the same meaning as above, and/or with another ketone of formula $R^5$—CO—$R^5$, in which $R^5$ and $R^6$, which are identical or different, have the same meaning as above.

The ketone $R^3$—CO—$R^4$ is preferably chosen from those in which $R^3$ or $R^4$ represents a methyl radical, such as, in particular, acetone, ethyl methyl ketone or methyl propyl ketone.

The aldehyde $R^1$—CHO is advantageously chosen from ethanal, propanal, butanal, isobutanal, pentanal, hexenal and heptenal.

The aldehyde $R^2$—CHO is advantageously chosen from methanal, ethanal, propanal, butanal, isobutanal and benzaldehyde. Use is preferably made of methanal, butanal and isobutanal.

The compounds of formula (I) are used in particular in the preparation of β-hydroxycarbonyl and α,β-unsaturated carbonyl compounds, such as mesityl oxide, 2-ethyl-2-hexenal, 5-methyl-3-hexen-2-one, 3-hepten-2-one, 2,2,4-trimethyl-3-hydroxypentanal or 2-ethyl-3-hydroxyhexanal, and very particularly in the preparation of diacetone alcohol (4-hydroxy-4-methyl-2-pentanone) from acetone by basic heterogeneous catalysis according to the reaction:

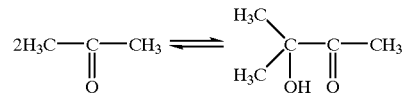

This is an equilibrium reaction; the concentration at equilibrium at 0° C. is 23.1% and decreases when the temperature increases.

In addition, when the temperature increases, the selectivity for diacetone alcohol falls as a result of dehydration and polycondensation reactions, the said reactions resulting in the formation of mesityl oxide, tridiacetone alcohol and phorone.

The β-hydroxycarbonyl and/or α,β-unsaturated carbonyl compounds can be obtained continuously or batchwise according to operating conditions (temperatures, pressures, and the like) known to a person skilled in the art.

When the reaction is carried out batchwise, the amount of compound (I) according to the invention used with respect to the total charge of reactants introduced into the reactor is generally between approximately 0.5% and approximately 20% and preferably between approximately 2% and approximately 15%.

A ratio by mass of compound (I) used to the total charge of reactants introduced of between approximately 3% and approximately 10% is particularly preferred.

As regards the production of diacetone alcohol, the reaction can be carried out in a stationary bed or in a stirred bed at a reduced temperature, so as to promote the formation of diacetone alcohol. The reaction will be carried out at a temperature at most equal to 10° C. and preferably of between 0° C. and 5° C.

In the eventuality of the reaction being carried out in a stirred bed, use will be made of amounts by weight of compound of formula (I) ranging from 5% to 10% with respect to the acetone employed.

The use of the compounds of formula (I) as basic catalysts exhibits the advantage of resulting selectively in β-hydroxycarbonyl and/or α,β-unsaturated carbonyl compounds with a high conversion.

The examples which follow illustrate the invention.

Preparation of an Activated Nickel Aluminium Hydrotalcite.

Synthesis of the hydrotalcite:

600 ml of an aqueous sodium bicarbonate solution are introduced, with stirring and at room temperature, into a two liter reactor, which is open to the air, equipped with a stirrer and a reflux condenser. The amount of bicarbonate is controlled in order to obtain a pH of 8. 400 ml of an aqueous solution comprising 0.3 ml of nickel nitrate and 0.1 mol of aluminium chloride are then introduced using a pump. The throughput of the pump is between 3 and 6 ml/min. During this addition, the pH is maintained at 8 by addition of a 3N sodium hydroxide solution.

At the end of the introduction, the mixture is brought to reflux (100° C.), still with stirring. Reflux is maintained for approximately 18 hours.

The mixture is then cooled and the solid is filtered off and washed with water until the aqueous wash liquors are free from chlorides.

The product obtained is green and has the following formula:

$$Ni_{0.75}Al_{0.25}(OH)_2(CO_3^{2-})_{0.172}\cdot mH_2O$$

Exchange with carbonate:

This product is exchanged as follows: 2 grams of hydrotalcite prepared above are added to a solution of 0.69 g of $Na_2CO_3$ in 100 ml of distilled water. The suspension is brought to 80° C. with stirring for three hours. The solid is filtered off and then washed twice with water. A second exchange is carried out in the same way. A solid is obtained in which it is impossible to titrate chloride by potentiometry (argentometry in nitric acid medium in which the hydrotalcite is soluble).

Calcination:

The exchange solid is calcined under dry air according to the following thermal programme:

rise to 450° C. over 5 hours, stationary phase at 450° C. for 10 hours, free cooling, still while flushing with dry air.

The weight of calcined solid represents 60 to 65% of the weight of starting solid.

The mixed oxide is black.

Activation:

The solid is suspended in 100 g of decarbonated water and then the suspension is introduced into an autoclave lined with Teflon. The suspension is brought to 120° C. for 48 hours.

The solid is recovered green.

A compound is obtained of formula:

$$Ni_{0.75}Al_{0.25}(OH)_{2.25}\cdot mH_2O$$

Preparation of an Activated Zinc Aluminium Hydrotalcite.

Synthesis of the hydrotalcite:

600 ml of an aqueous sodium bicarbonate solution are introduced, with stirring and at room temperature, into an open two-liter reactor equipped with a stirrer and a reflux condenser. The amount of bicarbonate is controlled in order to obtain a pH of 8. 400 ml of an aqueous solution comprising 0.3 mol of zinc chloride and 0.1 mol of aluminium chloride are then introduced using a pump. The throughput of the pump is between 3 and 6 ml/min. During this addition, the pH is adjusted to 8 by addition of a 3N sodium hydroxide solution.

At the end of the introduction, the mixture is brought to reflux (100° C.), still with stirring. Reflux is maintained for approximately 18 hours.

The mixture is then cooled and the solid is filtered off and washed with water until the aqueous wash liquors are free from chlorides.

The product obtained has the following formula:

$$Zn_{0.76}Al_{0.24}(OH)_2(CO_3^{2-})_{0.14}\cdot mH_2O$$

Exchange with carbonate:

This product is exchanged twice as follows: 2 grams of hydrotalcite prepared above are added to a solution of 0.69 g of $Na_2CO_3$ in 100 ml of distilled water. The suspension is brought to 80° C. with stirring for 3 hours. The solid is filtered off and then washed twice with water. A second exchange is carried out in the same way. A solid is obtained in which it is impossible to titrate chloride by potentiometry.

Calcination:

The exchanged solid is calcined under dry air according to the following thermal programme:

rise to 450° C. over 5 hours, stationary phase at 450° C. for 10 hours, free cooling, still while flushing with dry air.

Activation:

The solid is suspended in 100 g of decarbonated water at 80° C. The suspension is maintained at 80° C. for 8 hours.

A compound is obtained of formula:

$$Zn_{0.76}Al_{0.24}(OH)_{2.24}\cdot mH_2O$$

Preparation of an Activated Nickel Gallium Hydrotalcite.

Synthesis of the hydrotalcite:

It is carried out according to conditions identical to those used to prepare the above hydrotalcites.

The product obtained has the following formula:

$$Ni_{0.78}Ga_{0.22}(OH)_2(CO_3^{2-})_{0.146}\cdot 0.76H_2O$$

The exchange with carbonate, the calcination and the activation are carried out according to the same conditions identical to those used to prepare the activated zinc aluminium or nickel aluminium hydrotalcites.

A compound is obtained of formula:

$$Ni_{0.78}Ga_{0.22}(OH)_{2.22}\cdot mH_2O$$

Use of the Activated Hydrotalcites Prepared above in the Synthesis of Diacetone Alcohol:

TEST 1

100 g of acetone are introduced into a stirred 500 ml reactor equipped with a reflux condenser, a system for inerting with nitrogen and a jacket allowing thermostatic control by circulation of a thermal fluid. The acetone is brought to 0° C. with stirring while purging the head space of the reactor with nitrogen.

when the temperature is stabilized, 3 g of wet activated nickel aluminium hydrotalcite prepared above are introduced while avoiding, as far as possible, any contact of the latter with the air.

Rinsing is carried out four times with 100 g of acetone.

Reaction is allowed to take place with stirring. A sample is regularly withdrawn and analysed by gas chromatography (GC) on a Hewlett-Packard 6890 chromatography. The formation of diacetone alcohol, mesityl oxide and tridiacetone alcohol is thus monitored.

The characteristics of the GC analysis are as follows:

Hewlett-Packard Carbowax 20 M capillary column having a length of 30 m and a diameter of 1.33 μm, detector: thermal conductivity cell, carrier gas: helium (flow rate: 20 ml/s), injector temperature: 150° C., detector temperature: 180° C., temperature of the column: 5 minutes at 50° C. and then 8° C./min up to 200° C.

Under these analytical conditions, neither mesityl oxide nor tridiacetone dialcohol is detected.

The percentage by weight of diacetone alcohol (DAA) obtained is listed in Table 1 below as a function of the reaction duration.

TABLE 1

| DURATION (MIN) | % OF DAA |
|---|---|
| 0 | 0 |
| 20 | 6.5 |
| 60 | 10.5 |
| 120 | 12.9 |
| 180 | 14.5 |
| 240 | 15.45 |
| 1320 | 20.4 |

TEST 2

The reaction is carried out as in Test 1, except that 2.8 g of activated zinc aluminium hydrotalcite as prepared above are used.

the percentage by weight of diacetone alcohol (DAA) obtained is listed in Table 2 as a function of the reaction duration.

TABLE 2

| DURATION (MIN) | % OF DAA |
|---|---|
| 0 | 0 |
| 20 | 0.33 |
| 240 | 1.8 |
| 1320 | 4.3 |

It should be noted that, in this test also, mesityl oxide and tridiacetone alcohol were not detected under the GC analytical conditions as mentioned above.

TEST 3

The reaction is carried out as in Test 1, except that 2.8 g of activated nickel gallium hydrotalcite as prepared above are used.

The percentage by weight of diacetone alcohol (DAA) obtained is listed in Table 3 as a function of the reaction duration.

TABLE 3

| DURATION (MIN) | % OF DAA |
|---|---|
| 0 | 0 |
| 20 | 8.5 |
| 60 | 12.6 |
| 120 | 14.3 |
| 180 | 16.3 |
| 1320 | 21.1 |

Recycling test:

The nickel aluminium hydrotalcite used in Test 1 was reused once in the synthesis of diacetone alcohol according to conditions identical to those of Test 1, with a mass of nickel aluminium hydrotalcite of 3 g, as in Test 1.

The results are listed in Table 4. In this table, the percentage by weight of diacetone alcohol (DAA) obtained with the nickel aluminium hydrotalcite used in Test 1 (Test 1) and with the same hydrotalcite reused once (recycling) is listed as a function of the reaction duration.

TABLE 4

| DURATION | % OF DAA | |
|---|---|---|
| (MIN) | TEST 1 | RECYCLING |
| 0 | 0 | 1.5(1) |
| 20 | 6.5 | 7.5 |
| 60 | 10.5 | 11 |
| 120 | 12.9 | 13 |
| 180 | 14.5 | not measured |
| 240 | 15.45 | 15.6 |
| 1320 | 20.4 | |

(1) The initial value is not zero because the recycling test is carried out with the heel from Test 1 (catalyst plus reaction mixture plus 100 g of fresh acetone).

It is found that the recycling does not result in a loss in activity of the catalyst.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding French application No. 97/15390, filed Dec. 5, 1997 is hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. In a process comprising reacting acetone by basic heterogeous catalysis to obtain diacetone alcohol, the improvement wherein the catalyst is a compound with a hydrotalcite structure of the formula:

$$[M(II)_{1-x}M(III)_x(OH)_{2-x}] \cdot mH_2O \qquad (I)$$

in which M(II) represents at least one divalent cation chosen from the group consisting of nickel, zinc, cobalt, and magnesium; M(III) represents aluminium, gallium, iron or chromium, with the exception that when M(II) is magnesium M(III) is not aluminium; x is between 0.20 and 0.33; and m≦1, and said reacting is conducted at a temperature not higher than 10° C.

2. A process according to claim 1, wherein, in the compound of formula (I), M(II) is nickel or zinc and M(III) is aluminium or gallium.

3. A process according to claim 1, wherein, in the compound of formula (I), M(II) is nickel or zinc and M(III) is aluminium.

4. A process according to claim 1, wherein, in the compound of formula (I), M(II) is zinc and M(III) is aluminum.

5. A process according to claim 1, wherein, in the compound of formula (I), M(II) is nickel and M(III) is gallium.

6. A process according to claim 1, wherein, in the compound of formula (I), M(II) is magnesium and M(III) is gallium.

7. A process according to claim 1, wherein the reaction is conducted at a temperature of between 0° C. and 5° C.

8. A process according to claim 1, wherein said reacting is conducted under conditions resulting in the production of said diacetone alcohol in the absence of detectable amounts of mesityl oxide and tridiacetone dialcohol.

9. A process according to claim 1, wherein the catalyst is $Ni_{0.75}Al_{0.25}(OH)_{2.25} \cdot mH_2O$.

10. A process according to claim 1, wherein the catalyst is $Zn_{0.76}Al_{0.24}(OH)_{2.24} \cdot mH_2O$.

11. A process according to claim 1, wherein the catalyst is $Ni_{0.78}Ga_{0.22}(OH)_{2.22} \cdot mH_2O$.

* * * * *